United States Patent
Choi et al.

(10) Patent No.: US 8,469,587 B2
(45) Date of Patent: Jun. 25, 2013

(54) APPARATUS AND METHOD FOR MEASURING CONVECTIVE HEAT TRANSFER COEFFICIENTS OF NANOFLUIDS

(75) Inventors: Cheol Choi, Daejeon (KR); Je-Myung Oh, Daejeon (KR); Mi-Hee Jung, Daejeon (KR); Shin-Pyo Lee, Gyeonggi-do (KR)

(73) Assignee: Korea Electric Power Corporation, Seoul (KR)

( * ) Notice: Subject to any disclaimer, the term of this patent is extended or adjusted under 35 U.S.C. 154(b) by 502 days.

(21) Appl. No.: 12/609,183

(22) Filed: Oct. 30, 2009

(65) Prior Publication Data

US 2010/0329299 A1    Dec. 30, 2010

(30) Foreign Application Priority Data

Jun. 30, 2009 (KR) .......... 10-2009-0059460
Sep. 25, 2009 (KR) .......... 10-2009-0090765

(51) Int. Cl.
G01N 25/20 (2006.01)
(52) U.S. Cl.
USPC ............ 374/43; 374/44; 73/204.27
(58) Field of Classification Search
USPC .......... 374/43, 39, 45, 49, 55, 51, 187
See application file for complete search history.

(56) References Cited

U.S. PATENT DOCUMENTS

| | | | | |
|---|---|---|---|---|
| 2,769,334 A | * | 11/1956 | Soehngen | 374/43 |
| 3,480,002 A | * | 11/1969 | O'Connor et al. | 600/445 |
| 4,170,144 A | * | 10/1979 | Scott | 73/609 |
| 5,948,360 A | * | 9/1999 | Rao et al. | 422/65 |
| 7,160,511 B2 | * | 1/2007 | Takahashi et al. | 422/504 |

OTHER PUBLICATIONS

Shinpo Lee, "Measuring Convective Heat Transfer Coefficient Around a Heated Fine Wire in Cross Flow of Nanofluids," 2008; w/ English abstract thereof.
Changhwan Cho et al., "Thermal Conductivity measurement of Binary Nanofluids by the Transient Hot-wire Method," 2008; w/ English abstract thereof.

* cited by examiner

Primary Examiner — Lisa Caputo
Assistant Examiner — Roger Hernandez-Prewitt
(74) Attorney, Agent, or Firm — McDermott Will & Emery LLP

(57) ABSTRACT

The present invention relates to an apparatus and method for measuring the convective heat transfer coefficients of nanofluids, which can realize a small-sized structure and can accurately control the movement velocity of a hot wire sensor within a fluid. The apparatus for measuring the convective heat transfer coefficients of nanofluids according to the present invention includes a sensor unit, a transfer unit and a liquid container. The transfer unit is formed on the sensor unit and is configured to allow the sensor unit to longitudinally reciprocate in a direction parallel to a ground surface with the sensor unit spaced apart from the ground surface. The liquid container is arranged below and spaced apart from the sensor unit, and is configured to allow a nanofluid or a base fluid, a convective heat transfer coefficient of which needs to be measured, to be put therein.

10 Claims, 10 Drawing Sheets

APPARATUS AND METHOD FOR MEASURING CONVECTIVE HEAT TRANSFER COEFFICIENTS OF NANOFLUIDS

CROSS-REFERENCE TO RELATED PATENT APPLICATION

This application claims the benefit of Korean Patent Application Nos. 10-2009-0059460, filed on Jun. 30, 2009 & 10-2009-0090765, filed on Sep. 25, 2009, in the Korean Intellectual Property Office, the disclosure of which is incorporated herein in its entirety by reference.

BACKGROUND OF THE INVENTION

1. Field of the Invention

The present invention relates to an apparatus and method for measuring the convective heat transfer coefficients of nanofluids.

2. Description of the Related Art

A nanofluid is a mixed fluid configured to add a small quantity of nano-sized solid particles having very high thermal conductivity to a base fluid, such as water or ethylene glycol, for heat transfer purposes, thereby increasing the thermal conductivity of the fluid, with the result that the overall heat transfer performance is improved. Therefore, the degree of improvement of heat transfer performance of a nanofluid appearing after the mixing of the particles, compared to that of the initial base fluid, must be quantitatively measured.

The determination of thermal performance of a nanofluid in conventional technology was conducted in such a way as to measure thermal conductivity in a static state and to primarily determine whether there is a possibility of improving heat transfer performance of the nanofluid. However, the addition of nanoparticles to a fluid generally accompanies an increase in viscosity along with an improvement of thermal conductivity. Due thereto, the thermal conductivity of a nanofluid is improved, but more pump power may be required to drive such a nanofluid. A nanofluid is a medium to be used in a convective heat transfer state, that is, in the state in which the flow of a fluid is present. According to the theory of convective heat transfer, thermal conductivity is one of a plurality of variables influencing convective heat transfer, and thus determining the performance of a nanofluid by measuring only thermal conductivity results in a plurality of problems in actual application. Therefore, in order to determine the ultimate thermal performance of a nanofluid, an experiment for measuring a convective heat transfer coefficient is required.

A representative experimental device for measuring a convective heat transfer coefficient may be a double pipe heat exchanger or an internal flow device using a heated pipe. However, since this experimental device also includes peripheral devices such as a thermostat and a pump, it has a complicated structure and a large size. Therefore, many difficulties are encountered in the evaluation of the convective heat transfer performance of a nanofluid. Further, unlike the measurement of thermal conductivity performed in a static state, the convective heat transfer experiment is problematic in that a lot of cost and time is required, and large errors may be included in the ultimately calculated convective heat transfer coefficient depending on the circumstances.

In detail, the conventional convective heat transfer experiment is problematic in that a lot of manufacturing time and cost is required in order to acquire an amount of nanofluid sample sufficient to fill the inside of the device, and in that, when it is desired to replace a sample, it is difficult to wash the inside of the device. Further, there is an additional problem in that, when the precision of acquired data and heat loss occurring in a measurement procedure are not accurately calculated, uncertainty included in a convective heat transfer coefficient increases. Furthermore, such a conventional convective heat transfer experiment is also problematic in that, when samples must be discarded, additional cost and environmental pollution occur.

SUMMARY OF THE INVENTION

Accordingly, the present invention has been made keeping in mind the above problems occurring in the prior art, and an object of the present invention is to provide an apparatus and method for measuring the convective heat transfer coefficients of nanofluids, which can realize a small-sized structure and can accurately control the movement velocity of a hot wire sensor within a fluid.

In order to accomplish the above object, the present invention provides an apparatus for measuring convective heat transfer coefficients of nanofluids, comprising a sensor unit; a transfer unit formed on the sensor unit and configured to allow the sensor unit to longitudinally reciprocate in a direction parallel to a ground surface with the sensor unit spaced apart from the ground surface; and a liquid container arranged below and spaced apart from the sensor unit, and configured to allow a nanofluid or a base fluid, a convective heat transfer coefficient of which needs to be measured, to be put therein.

Preferably, the sensor unit comprises a hot wire sensor implemented as a metallic hot wire formed in a cylindrical shape; a hot wire sensor holder connected to both ends of the hot wire sensor and configured to hold the hot wire sensor in a state parallel to the ground surface; a sensor unit body formed on the hot wire sensor holder and formed to have a shape of a bar equipped with hollow spaces therein; and a support formed to extend upwards from the sensor unit body and configured to connect the sensor unit body to the transfer unit and support both the sensor unit body and the transfer unit.

Preferably, the sensor unit further comprises a standard resistor electrically connected to the hot wire sensor; and a power source configured to supply current both to the standard resistor and to the hot wire sensor.

Preferably, the sensor unit further comprises a data processing device capable of acquiring and storing data measured at the hot wire sensor.

Preferably, the hot wire sensor is coated with Teflon.

Preferably, the hot wire sensor is a platinum hot wire or a tungsten hot wire.

Preferably, the transfer unit comprises a transfer unit body longitudinally formed parallel to the ground surface; a movable block connected to the sensor unit and configured to longitudinally reciprocate in a direction parallel to the ground surface along the transfer unit body; a motor formed at one end of the transfer unit body and configured to reciprocate the movable block by forward/reverse rotation of the motor; and a motor controller electrically connected to the motor and configured to control rotational speed and rotational direction of the motor.

Preferably, the transfer unit body comprises a screw formed in a shape of a cylinder, a surface of which has a spiral protrusion, and configured to be forwardly/reversely rotated by the motor; and a guide plate arranged in parallel below and spaced apart from the screw and formed in a shape of a plate.

Preferably, the apparatus further comprises a heat-shielding device provided outside the liquid container.

Further, in order to accomplish the above object, the present invention provides a method of measuring convective heat transfer coefficients of nanofluids, comprising the steps of a liquid preparation step of putting a base fluid or a nanofluid in a liquid container; a sensor unit setting step of operating a power source of a voltage dividing circuit and a data processing device electrically connected to a hot wire sensor of a sensor unit; a motor driving step of driving a motor of a transfer unit to longitudinally reciprocate the hot wire sensor in a direction parallel to a ground surface, with the hot wire sensor being soaked in the base fluid or the nanofluid put in the liquid container; a motor driving stop and power interruption step of stopping driving of the motor and interrupting supply of power to the voltage dividing circuit; and a data processing step of analyzing and processing data acquired by the data processing device.

Preferably, the voltage dividing circuit comprises a power source electrically connected to the hot wire sensor and configured to supply the power to the hot wire sensor; and a standard resistor electrically connected in series with the hot wire sensor and the power source.

Preferably, the motor driving step is performed such that speed of forward/reverse rotation of the motor can be accurately controlled by a motor controller electrically connected to the motor.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Embodiments of the present invention will be described in detail to such an extent that those skilled in the art can easily implement the present invention with reference to the attached drawings.

Hereinafter, an apparatus for measuring the convective heat transfer coefficients of nanofluids according to the present invention will be described.

Figure 1:
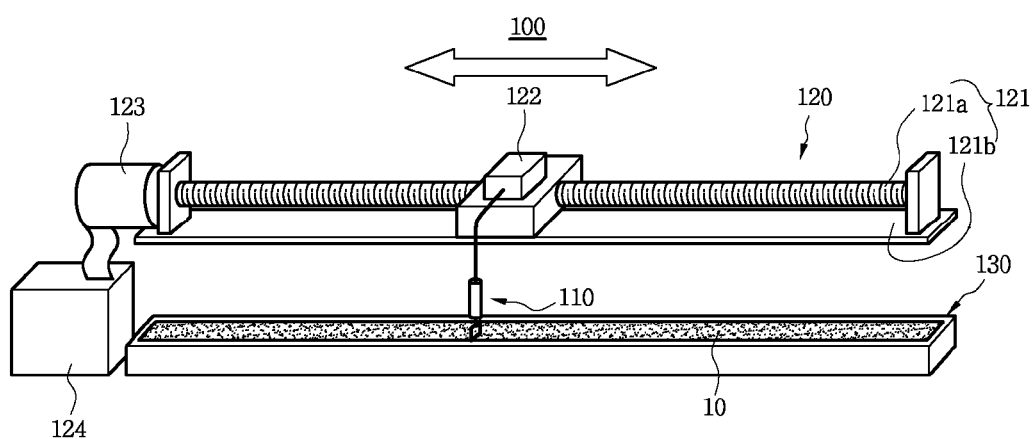
FIG. 1 is a diagram showing the schematic construction of an apparatus for measuring the convective heat transfer coefficients of nanofluids according to the present invention.

FIG. 1 is a diagram showing the schematic construction of an apparatus for measuring the convective heat transfer coefficients of nanofluids according to the present invention.

A convective heat transfer coefficient measurement apparatus 100 according to the present invention includes a sensor unit 110, a transfer unit 120 formed at one end of the sensor unit 110, and a liquid container 130 arranged below and spaced apart from the sensor unit 110.

A lower portion of the sensor unit 110 is being soaked in a base fluid or nanofluid 10 so as to measure the convective heat transfer coefficient of the base fluid or nanofluid 10. Further, unlike a conventional scheme for determining whether a possibility of improving the heat transfer performance of a nanofluid in a static state is present, the apparatus 100 of the present invention is configured such that the sensor unit 110 performs dynamic movement, with the lower portion of the sensor unit 110 being soaked in the base fluid or nanofluid 10. Accordingly, the present invention can determine the convective heat transfer coefficient of the nanofluid in a dynamic state. The sensor unit 110 may include a voltage dividing circuit (not shown), including both a standard resistor and a power source, that is, a constant voltage device, and a data processing device (not shown) capable of acquiring measured data and processing the data. A detailed description of the sensor unit 110 will be made with reference to FIG. 2.

The transfer unit 120 may include a transfer unit body 121, a movable block 122 connected to the sensor unit 110 and configured to reciprocate along the transfer unit body 121, a motor 123 formed at one end of the transfer unit body 121, and a motor controller 124 formed at one end of the motor.

The transfer unit body 121 may be formed to include a screw 121a and a guide plate 121b.

The screw 121a may be formed in the shape of a cylinder, the surface of which has a spiral protrusion. Further, the screw 121a may be formed to be parallel to a ground surface. Furthermore, the screw 121a may be forwardly/reversely rotated by a driving means provided at one end of the transfer unit body 121.

The guide plate 121b may be formed in the shape of a plate. Further, the guide plate 121b may be arranged in parallel below and spaced apart from the screw 121a. Furthermore, the guide plate 121b may support the movable block 122 so that the movable block 122 can longitudinally reciprocate in a direction parallel to the ground surface along the screw 121a.

A cylindrical hollow space may be formed through the movable block 122 such that the movable block 122 is coupled to the transfer unit body 121 along the sides of the movable block 122 arranged in a direction of movement. A spiral protrusion to be engaged with the spiral protrusion of the screw 121a of the transfer unit body 121 may be formed on the inner circumference of the cylindrical hollow space of the movable block 122 so that the screw 121a and the movable block 122 are spirally coupled to each other. The sensor unit 110 may be formed on one side of the movable block 122, which is vertical to the direction of movement. Further, the movable block 122 may longitudinally reciprocate in a direction parallel to the ground surface along the transfer unit body 121 thanks to the rotation of the motor 123 formed at one end of the transfer unit body 121.

The motor 123 may be formed at one end of the transfer unit body 121. The motor 123 may rotate the screw 121a of the transfer unit body 121 to move the movable block 122. The motor controller 124 is electrically connected to one side of the motor 123. Further, the motor controller 124 is controlled by a computer, and is capable of accurately setting the rotational speed of the motor 123. As a result, the movement velocity of the movable block 122 can be accurately set. Therefore, conditions for the measurement of convective heat transfer coefficients may be clarified.

The liquid container 130 is arranged below and spaced apart from the sensor unit 110. Further, the liquid container 130 is configured such that a base fluid or nanofluid 10, the convective heat transfer coefficient of which needs to be measured, can be put therein. Furthermore, in the liquid container 130, the amount of the base fluid or nanofluid 10 can be adjusted so that the lower portion of the sensor unit 110 is being soaked in the base fluid or nanofluid 10. Since the liquid container 130 is separately arranged to be spaced apart from the sensor unit 110, it is easy to wash the liquid container 130 after measurement and replace and treat liquid samples to be measured. The apparatus 100 of the present invention may further include a heat-shielding device provided outside the liquid container 130 and configured to block the inflow of heat from the outside of the liquid container so as to systematically perform experiments concerning the variation in the convective heat transfer coefficient relative to variation in the temperature of a fluid.

Next, the sensor unit of the apparatus for measuring the convective heat transfer coefficients of nanofluids according to the present invention will be described below. In the description, the same reference numerals are used to designate components having the constructions or functions the same as those of the above embodiment. A description will be made on the basis of differences from the above embodiment.

Figure 2:
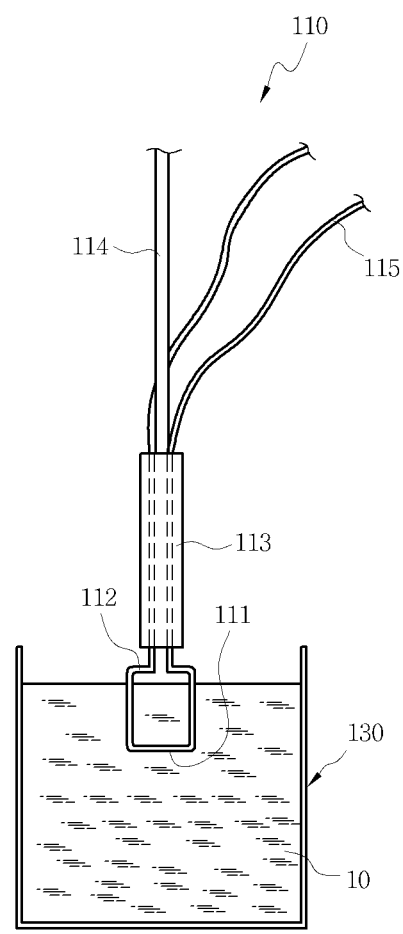
FIG. 2 is an enlarged diagram showing in detail the sensor unit of the apparatus for measuring the convective heat transfer coefficients of nanofluids according to the present invention.

FIG. 2 is an enlarged diagram showing in detail the sensor unit 110 of the apparatus for measuring the convective heat transfer coefficients of nanofluids according to the present invention.

The sensor unit 110 includes a hot wire sensor 111, a hot wire sensor holder 112 connected to both ends of the hot wire sensor and configured to hold the hot wire sensor 111, a sensor unit body 113 formed on the hot wire sensor holder 112, a support 114 formed to extend from the sensor unit body 113 and configured to connect the sensor unit body 113 to the transfer unit 120 and support the sensor unit body 113 and the transfer unit 120, and electrically conductive wires 115 electrically connected to the hot wire sensor 111.

The hot wire sensor 111 is a metallic hot wire which may be formed in a cylindrical shape. The hot wire sensor 111 operates as a metal resistor from the standpoint of an equivalent circuit. Further, the hot wire sensor 111 may correspond to a very small cylinder. Furthermore, the hot wire sensor 111 may be a platinum wire or a tungsten wire. The reason for this is that the platinum wire and the tungsten wire may be implemented as wires which withstand high temperature very well and are uniformly thin, and may desirably measure minute phenomena having small variations in time. In addition, the hot wire sensor 111 may have a surface coated with Teflon so as to test an electrically conductive fluid or a highly corrosive fluid.

The hot wire sensor holder 112 may be connected to both ends of the hot wire sensor 111 and configured to hold the hot wire sensor 111 in a state parallel to the ground surface.

Further, the inside of the hot wire sensor holder 112 may be electrically connected to the hot wire sensor 111. Furthermore, the surface of the hot wire sensor holder 112 may be formed as an insulator.

The sensor unit body 113 is formed on the hot wire sensor holder 112. The sensor unit body 113 may have the shape of a bar in which internal hollow spaces enabling the electrically conductive wires 115 to pass therethrough are formed.

The support 114 is formed to extend upwards from the sensor unit body 113. Further, the support 114 may be formed such that the other end thereof is connected to the movable block 122.

The electrically conductive wires 115 may be electrically connected to the hot wire sensor 111 and the inside of the hot wire sensor holder 112. Further, the electrically conductive wires 115 may be electrically connected to the voltage dividing circuit, the data processing device, etc. Meanwhile, the sensor unit 110 longitudinally reciprocates in a direction parallel to the ground surface. In this case, the electrically conductive wires 115 may pass through the internal hollow spaces of the sensor unit body 113 so that the electrically conductive wires 115 are not twisted.

Next, a method of measuring the convective heat transfer coefficient of a fluid, flowing around a hot wire sensor using the apparatus for measuring the convective heat transfer coefficients of nanofluids according to the present invention will be described below.

Figure 3:
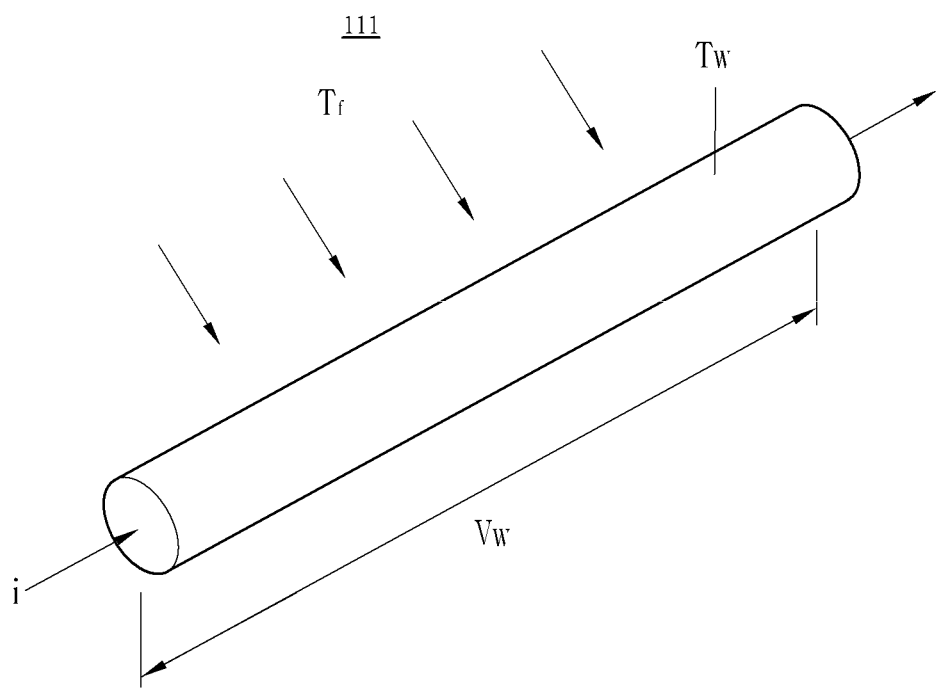
FIG. 3 is a diagram schematically showing a heated hot wire sensor and the convective heat transfer phenomenon of a fluid flowing around the sensor.
Figure 4:
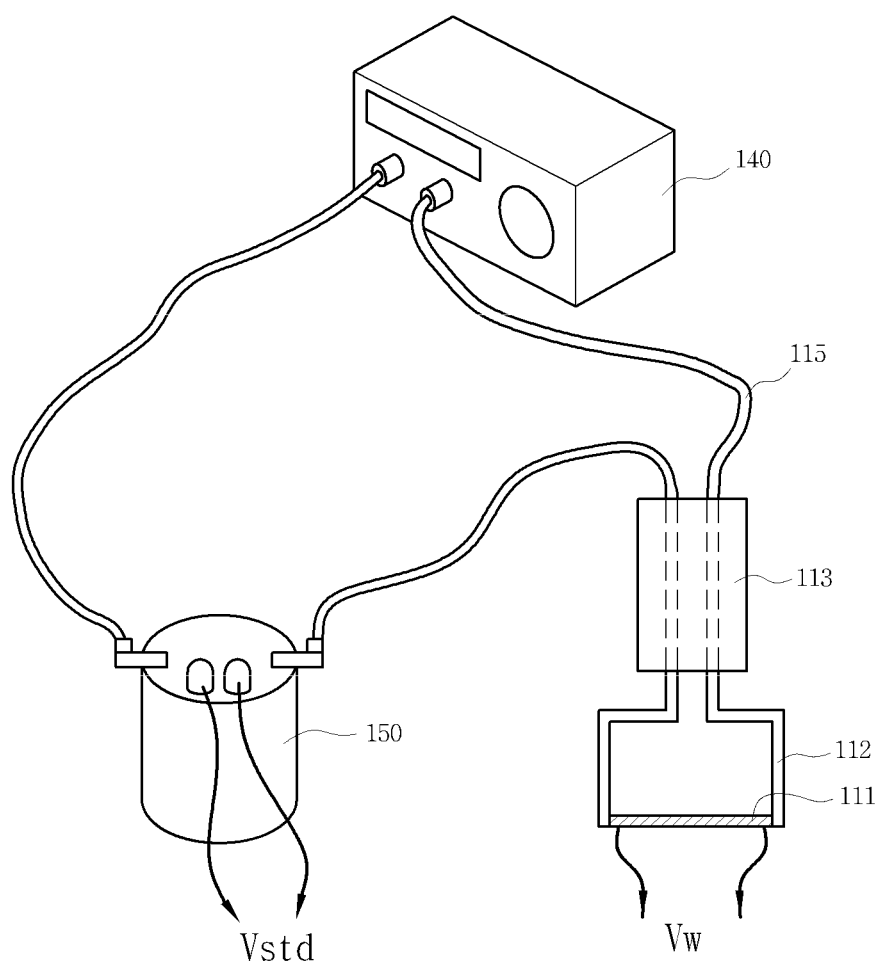
FIG. 4 is a diagram showing the schematic construction of a voltage dividing circuit in which a standard resistor and a hot wire sensor are connected to a power source.
Figure 5:
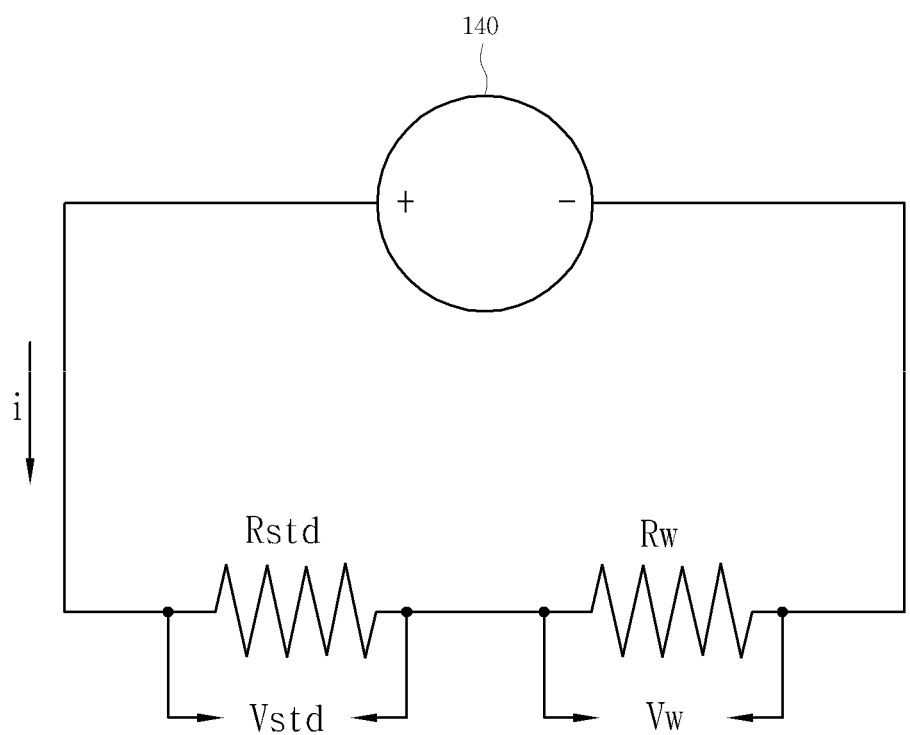
FIG. 5 is a circuit diagram showing an equivalent circuit of the voltage dividing circuit of FIG. 4.

FIG. 3 is a diagram schematically showing a heated hot wire sensor and the convective heat transfer phenomenon of a fluid flowing around the hot wire sensor. FIG. 4 is a diagram showing the schematic construction of a voltage dividing circuit in which a standard resistor and a hot wire sensor are connected to a power source. FIG. 5 is a circuit diagram showing an equivalent circuit of the voltage dividing circuit of FIG. 4.

Referring to FIG. 3, i is defined as a current flowing through the hot wire sensor 111, $V_w$ as a voltage across both ends of the hot wire sensor 111, and A as the surface area of the hot wire sensor 111 exposed to an external fluid. Further, $T_f$ is defined as the temperature of the external fluid and $T_w$ is defined as the temperature of the hot wire sensor 111. Further, h is a convective heat transfer coefficient indicating the heat transfer performance of a fluid and varying according to the flow velocity and the type of fluid.

Voltage $V_w$ is applied to the hot wire sensor 111 put in the fluid. Then, current i which is the flow of electrons is generated by an external force, that is, the voltage. At this time, the motion of electrons is interfered with by collisions with atomic nuclei, bound electrons, and internal impurities which exist in the hot wire sensor 111. During a procedure in which the electrons overcome such an interference and progress in one direction, frictional heat and thermal vibration of atoms occur. In this way, the Joule heat q, which is heat generated in a conductor, is generated by the flow of current, and is then transferred to the fluid by convection.

When the quantity of heat generated in the hot wire sensor 111 and the convective heat transfer to the fluid are balanced, the following Equation (1) is realized.

$$q = V_w \cdot i = h \cdot A \cdot (T_w - T_f) \quad (1)$$

In Equation (1), it can be seen that the operating temperature $T_w$ of the hot wire sensor 111 is determined by the Joule heat q, the convective heat transfer coefficient h and the external fluid temperature $T_f$. Therefore, in the case where the Joule heat q is constant, when the flow condition of external heat around the hot wire sensor 111 varies and the convective heat transfer coefficient h increases, cooling is actively performed, and thus the temperature of the hot wire sensor 111 decreases.

In contrast, when voltage and current across both ends of the hot wire sensor 111 are measured, and then the quantity of heat generated, the temperature of the metallic hot wire and the temperature of the fluid around the metallic hot wire can be known, the convective heat transfer coefficient h can be converted into that of the following Equation (2) under the given condition.

$$h = \frac{q}{A(T_w - T_f)} \quad (2)$$

Further, the hot wire sensor 111 used in the embodiment of the present invention is a platinum wire, corresponding to a cylinder having a very small diameter. Since the hot wire sensor 111 can be implemented as a small-sized structure, the entire size of the apparatus for measuring the convective heat transfer coefficients of nanofluids may also be decreased.

The voltage $V_w$, the current i flowing through the hot wire sensor, and the operating temperature $T_w$ of the hot wire sensor must be known in order to convert the convective heat transfer coefficient h under a given heat flow condition. The temperature $T_f$ of the external fluid is measured using a standard thermometer before the experiment is performed. Referring to FIGS. 4 and 5, the above experimental values can be measured using the voltage dividing circuit electrically connected in series with the hot wire sensor 111.

A constant voltage is supplied from a power source 140, the resistance value of the standard resistor 150 is $R_{std}$, and a voltage at the standard resistor 150 is $V_{std}$. Since the standard resistor 150 and the hot wire sensor 111 are connected in series, current flowing through the standard resistor 150 and current flowing through the hot wire sensor 111 are identical to each other, and the following Equation (3) is established by Ohm's law.

$$\frac{V_w}{R_w} = \frac{V_{std}}{R_{std}} \quad (3)$$

When Equation (3) is converted, the resistance $R_w$ of the hot wire sensor 111 in operation can be obtained by the following Equation (4), $$R_w = \frac{V_w}{V_{std}} R_{std} \quad (4)$$

In other words, when voltage $V_{std}$, at both ends of the standard resistor 150 and voltage $V_w$, across both ends of the hot wire sensor 111 are measured, $R_w$ can be obtained using the known standard resistance $R_{std}$.

The resistance-temperature relation of the following Equation (5) is established between the resistance and temperature of the hot wire sensor 111, $$R_w = R_0(1 + \alpha T_w) \quad (5)$$

where $R_0$ is the resistance of the hot wire sensor 111 at 0° C., and $\alpha$ is a temperature-resistance coefficient and has a value of 0.0039092/° C. when the hot wire sensor 111 is made of platinum. When Equation (5) is arranged for the operating temperature $T_w$, the following Equation (6) is obtained.

$$T_w = \frac{(R_w - R_o)}{R_o \alpha} \quad (6)$$

Therefore, when the operating resistance $R_w$ is known, the operating temperature $T_w$ can be estimated using Equation (5).

Next, a method of measuring the convective heat transfer coefficients of nanofluids using the apparatus for measuring the convective heat transfer coefficients of nanofluids according to the present invention will be described.

Figure 6:
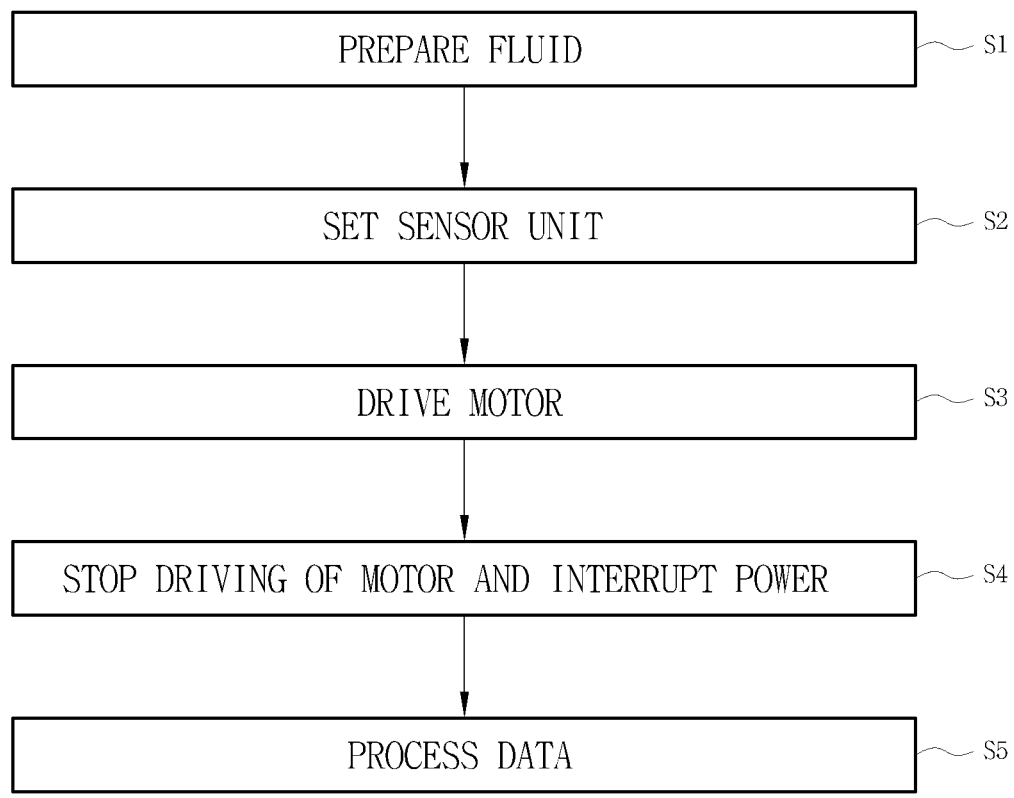
FIG. 6 is a flowchart showing a method of measuring the convective heat transfer coefficients of nanofluids according to the present invention.

FIG. 6 is a flowchart showing a method of measuring the convective heat transfer coefficients of nanofluids according to the present invention.

Referring to FIG. 6, the method of measuring the convective heat transfer coefficients of nanofluids according to the present invention may include a fluid preparation step S1, a sensor unit setting step S2, a motor driving step S3, a motor driving stop and power interruption step S4, and a data processing step S5.

The fluid preparation step S1 is the step of putting a base fluid or nanofluid, the convective heat transfer coefficient of which needs to be measured, in a liquid container to such an extent that a lower portion of the sensor unit of the apparatus for measuring the convective heat transfer coefficients of nanofluids is being soaked in the base fluid or nanofluid.

The sensor unit setting step S2 is the step of operating a voltage dividing circuit and a data processing device electrically connected to the hot wire sensor of the sensor unit of the apparatus for measuring the convective heat transfer coefficients of nanofluids. Further, in the voltage dividing circuit, a power source, that is, a constant voltage device, and a standard resistor may be electrically connected in series with the hot wire sensor. Further, the data processing device may measure the voltage across both ends of each of the standard resistor and the hot wire sensor.

The motor driving step S3 is the step of driving the motor so that the sensor unit longitudinally reciprocates in a direction parallel to the ground surface, with the lower portion of the sensor unit being soaked in the base fluid or nanofluid. Further, the motor driving step S3 enables a motor controller, electrically connected to one side of the motor to accurately control the speed of forward/reverse rotation of the motor, under the control of a computer. Furthermore, the movement velocity of the sensor unit can also be accurately controlled by accurately controlling the speed of the motor. Therefore, conditions for measurement of the convective heat transfer coefficient can be clarified, and data having repetitiveness and precision can be obtained.

The motor driving stop and power interruption step S4 is the step of stopping the driving of the motor and interrupting the power after a sufficient amount of data has been measured.

The data processing step S5 is the step of storing and processing the data acquired by the data processing device, thus calculating a convective heat transfer coefficient.

Next, data measured using the apparatus and method for measuring the convective heat transfer coefficients of nanofluids according to an embodiment of the present invention will be described below.

Figure 7:
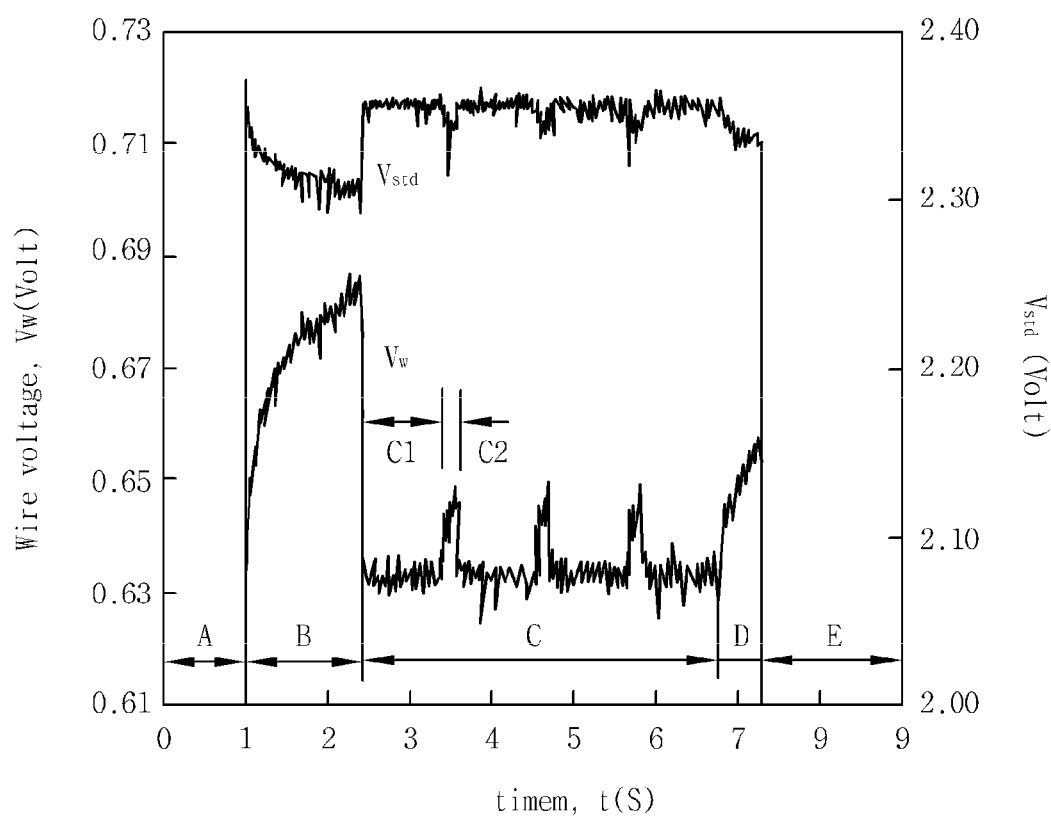
FIG. 7 is a diagram showing voltage signals measured at a standard resistor and a hot wire sensor according to an embodiment of the present invention.

FIG. 7 is a diagram showing voltage signals measured at a standard resistor and a hot wire sensor according to an embodiment of the present invention.

Referring to FIG. 7, a left vertical axis denotes the voltage $V_w$ across both ends of the hot wire sensor, a right vertical axis denotes the voltage $V_{std}$ at both ends of the standard resistor, and a horizontal axis denotes time t. In an experiment, 40 Ml engine oil was used as a fluid, and a platinum hot wire was used as the hot wire sensor.

The power of the voltage dividing circuit is about 3V. The sum of the voltage $V_w$ across both ends of the hot wire sensor of the left vertical axis and the voltage $V_{std}$, at both ends of the standard resistor of the right vertical axis, which are measured during the intervals B, C and D in which power is supplied, is 3V. The reason for this is that a voltage of 3V supplied from the power source has been divided and distributed depending on the relative magnitudes of the resistances of the hot wire sensor and the standard resistor. That is, although the resistance of the standard resistor is constant, the voltage $V_w$ across both ends of the hot wire sensor in a total voltage of 3V increases when the hot wire sensor is heated and the resistance thereof increases, whereas the voltage $V_{std}$ at both ends of the standard resistor decreases because the total voltage is the same. In contrast, when the hot wire sensor is cooled, the voltage $V_w$ across both ends of the hot wire sensor decreases, and the voltage $V_{std}$ at both ends of the standard resistor increases. Therefore, variation in the voltage $V_w$ at both ends of the hot wire sensor means variation in resistance, that is, variation in operating temperature.

Interval A indicates the state in which the voltage is not supplied by the power source, and the sensor unit of the apparatus for measuring the convective heat transfer coefficients of nanofluids according to the present invention does not move. Therefore, the voltage y, at both ends of the standard resistor and the voltage $V_w$ across both ends of the hot wire sensor are both 0.

Interval B indicates the state in which the voltage is supplied by the power source, but the sensor unit of the apparatus for measuring the convective heat transfer coefficients of nanofluids according to the present invention does not move. It can be seen that, as the voltage is supplied to the hot wire sensor by the power source, the temperature of the hot wire sensor increases, so that the resistance of the hot wire sensor increases, and the voltage $V_w$ across both ends of the hot wire sensor gradually increases, and the voltage $V_{std}$ at both ends of the standard resistor relatively decreases. Even in this case, the sum of the voltage $V_w$ across both ends of the hot wire sensor and the voltage $V_{std}$ at both ends of the standard resistor is identical to about 3V, that is, the voltage of the power source.

Interval C indicates the state in which the voltage is supplied by the power source, and the hot wire sensor of the sensor unit of the apparatus for measuring the convective heat transfer coefficients of nanofluids according to the present invention longitudinally reciprocates within the fluid in a direction parallel to the ground surface by means of the transfer unit. In this experiment, the hot wire sensor was set to reciprocate a distance of a total of 8 cm a total of four times for about four seconds total. In section C1, a constant voltage appears, which shows that the hot wire sensor was moved within the fluid at constant velocity. In section C2, it can be seen that the voltage $V_{std}$ at both ends of the standard resistor decreases, whereas the voltage $V_w$ across both ends of the hot wire sensor increases. The reason for this is that, in both end sections of each interval during which the hot wire sensor reciprocates, the movement velocity of the hot wire sensor is approximately 0, so that the cooling effect of the hot wire sensor by convective heat transfer is reduced, and the temperature of the hot wire sensor increases, and, as a result, the resistance of the hot wire sensor increases.

Interval D indicates the state in which the voltage is supplied by the power source, but the sensor unit of the apparatus for measuring the convective heat transfer coefficients of nanofluids according to the present invention does not move. Since the hot wire sensor does not move, and convective heat transfer to the surrounding fluid is not actively performed, the temperature of the hot wire sensor increases, and the resistance of the hot wire sensor increases. As a result, it can be seen that the voltage $V_w$ across both ends of the hot wire sensor increases, and the voltage $V_{std}$ at both ends of the standard resistor relatively decreases. Interval E indicates the interval in which the voltage is not supplied by the power source and the sensor unit of the apparatus for measuring the convective heat transfer coefficients of nanofluids according to the present invention does not move. Therefore, it can be seen that the voltage $V_w$ across both ends of the hot wire sensor and the voltage $V_{std}$ at both ends of the standard resistor are both 0.

Next, data measured by the apparatus and method for measuring the convective heat transfer coefficients of nanofluids according to another embodiment of the present invention will be described below.

Figure 8:
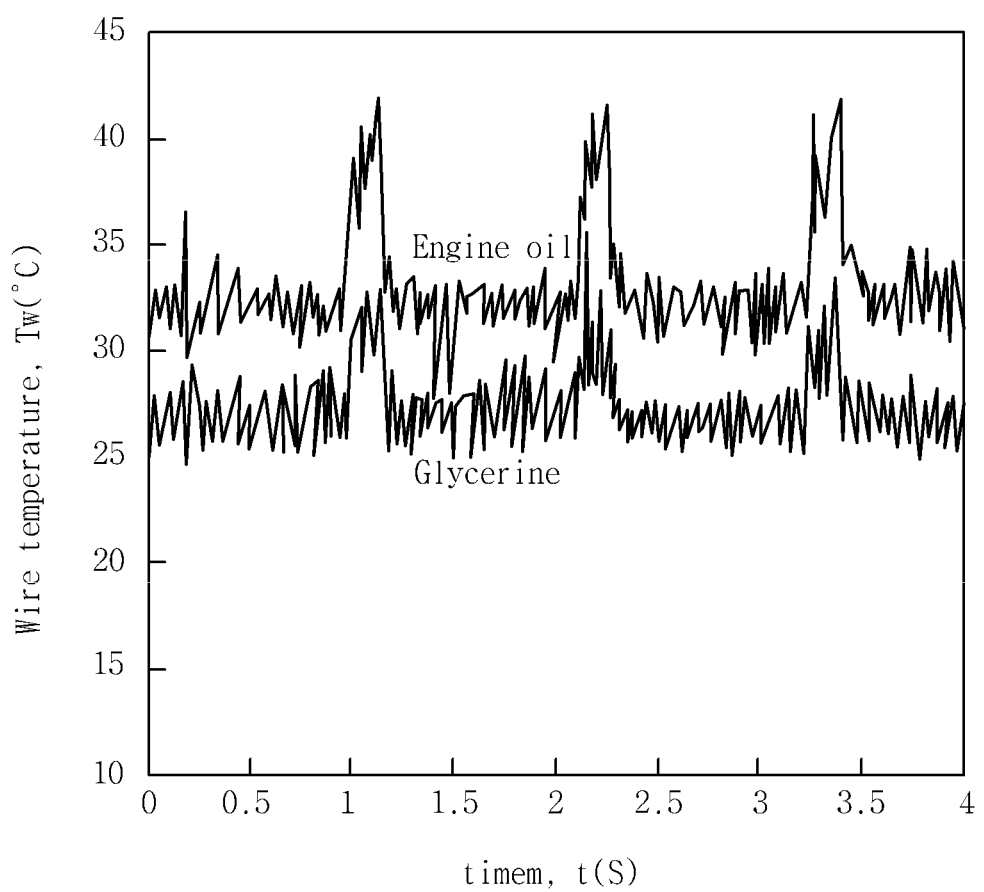
FIG. 8 is a diagram showing the temperatures of a hot wire sensor over time according to another embodiment of the present invention.
Figure 9:
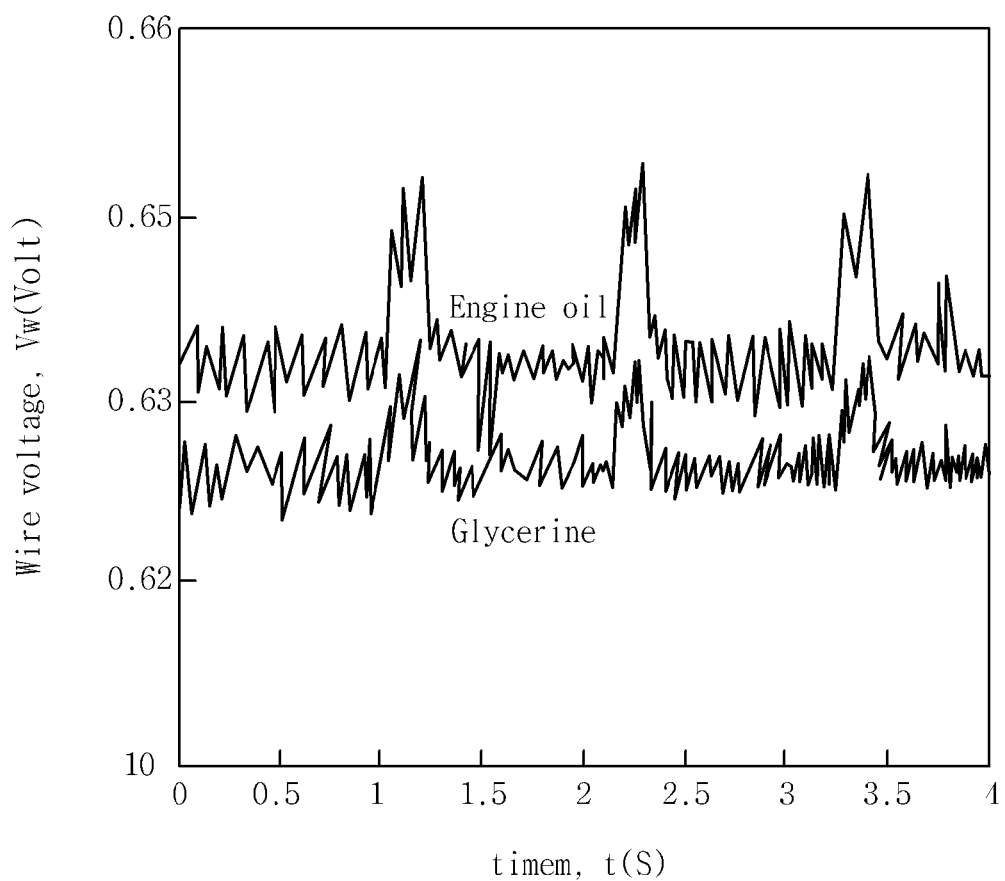
FIG. 9 is a diagram showing voltages at both ends of a hot wire sensor according to a further embodiment of the present invention.
Figure 10:
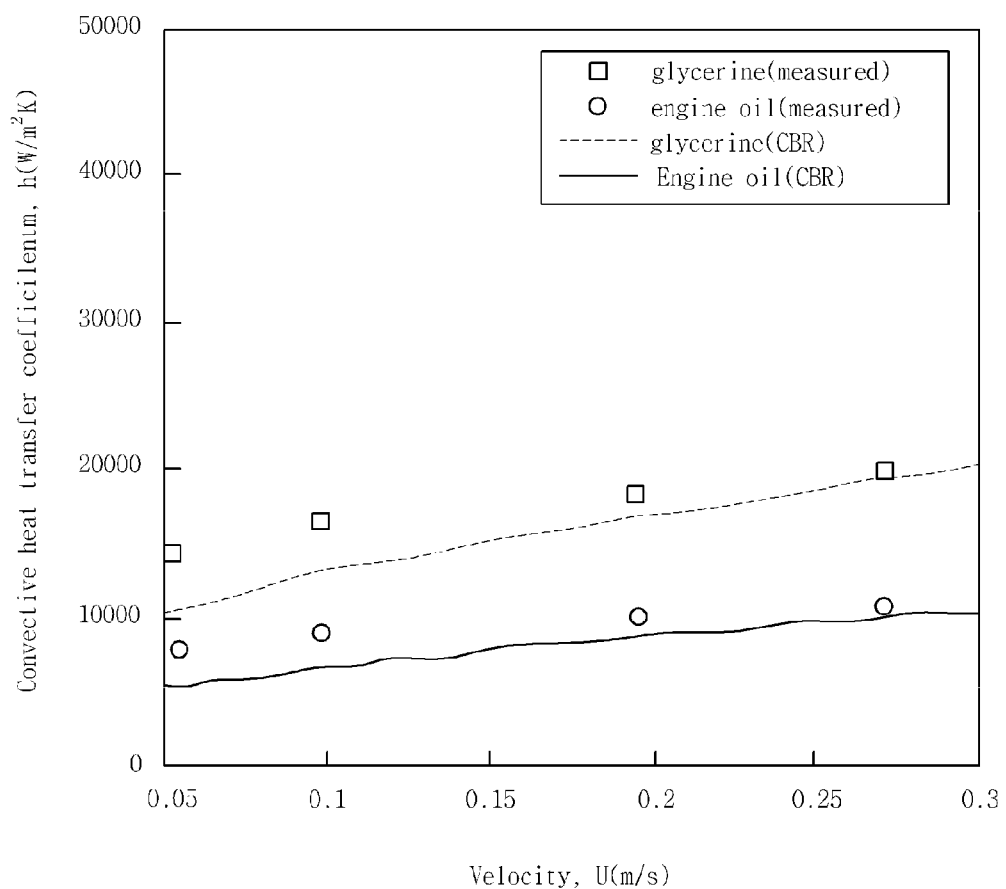
FIG. 10 is a diagram showing the comparison of measured values and theoretical values for the convective heat transfer coefficients of engine oil and glycerine relative to the velocity of a hot wire sensor according to yet another embodiment of the present invention.

FIG. 8 is a diagram showing the temperature of a hot wire sensor over time according to another embodiment of the present invention. FIG. 9 is a diagram showing the voltage across both ends of the hot wire sensor over time according to a further embodiment of the present invention. FIG. 10 is a diagram showing the comparison of measured values and theoretical values of convective heat transfer coefficients for engine oil and glycerine, relative to the velocity of a hot wire sensor according to yet another embodiment of the present invention.

Referring to FIG. 8, a left vertical axis denotes the temperature $T_w$ of the hot wire sensor, and a horizontal axis denotes time t. In this experiment, 40 Ml engine oil and 40 Ml glycerine were used as fluids, a platinum hot wire was used as the hot wire sensor, and the power of the voltage dividing circuit is about 3V. Further, the hot wire sensor of the apparatus for measuring the convective heat transfer coefficients of nanofluids according to the present invention was set to reciprocate a distance of a total of 8 cm a total of four times for about four seconds total. The measurement of data was initiated after the hot wire sensor of the apparatus for measuring convective heat transfer coefficients of nanofluids according to the present invention had been accelerated and the movement velocity of the hot wire sensor had become constant. An upper curve shows the temperature of the hot wire sensor when measurement was performed by using engine oil as a fluid, and a lower curve shows the temperature of the hot wire sensor when measurement was performed by using glycerine as a fluid. Both the graphs show that when the hot wire sensor moves at a constant velocity, it is maintained at a constant temperature, and that, in both end sections of each reciprocation interval, convective heat transfer does not desirably occur due to the stoppage of the hot wire sensor, and then the temperature of the hot wire sensor increases. In the case of engine oil, when the hot wire sensor moves at a constant velocity, that is, when the temperature of the hot wire sensor is maintained at a constant level in the graph, the temperature of the hot wire sensor within the engine oil is 31.9° C. Further, the temperature of the hot wire sensor within glycerine is about 26.8° C. Therefore, it can be seen that the temperature of the hot wire sensor within the engine oil fluid is higher than that within the glycerine. This shows that, since the convective heat transfer coefficient of the glycerine is greater than that of the engine oil, the cooling effect of the hot wire sensor within the glycerine is better than that within the engine oil.

Referring to FIG. 9, a left vertical axis denotes the voltage $V_w$ across both ends of the hot wire sensor, and a horizontal axis denotes time t. In this experiment, 40 Ml engine oil and 40 Ml glycerine were used as fluids, a platinum hot wire was used as a hot wire sensor, and the power of a voltage dividing circuit is about 3V. Further, the hot wire sensor of the apparatus for measuring the convective heat transfer coefficients of nanofluids according to the present invention was set to reciprocate a distance of a total of 8 cm a total of four times for about four seconds total. The measurement of data was initiated after the hot wire sensor of the apparatus for measuring the convective heat transfer coefficients of nanofluids according to the present invention had been accelerated and the movement velocity of the hot wire sensor had become constant. An upper curve shows the voltage across both ends of the hot wire sensor when measurement was performed by using the engine oil as a fluid, and a lower curve shows the voltage across both ends of the hot wire sensor when measurement was performed by using the glycerine as a fluid. The graph of FIG. 9 shows that the curves thereof are almost identical to those of the graph of FIG. 8 measured under the same experimental conditions. The reason for this is that, as the temperature of the hot wire sensor increases, the resistance thereof increases, and thus the voltage across both ends of the hot wire sensor also increases.

Referring to FIG. 10, a left vertical axis denotes a convective heat transfer coefficient h, and a horizontal axis denotes the velocity of the hot wire sensor within a fluid. A solid line and a dotted line denote existing convective heat transfer coefficients obtained by conventional heat transfer relations of engine oil and glycerine, respectively. Further, ○ and □ respectively denote the convective heat transfer coefficients of engine oil and glycerine measured and calculated by the apparatus for measuring the convective heat transfer coefficients of nanofluids according to the present invention. It can be seen from FIG. 10 that the measured convective heat transfer coefficients are almost identical to the existing theoretic values.

As described above, an apparatus and method for measuring the convective heat transfer coefficients of nanofluids according to the present invention enable convective heat transfer coefficients to be measured using a small amount of fluid sample, and thus convective heat transfer coefficients can be measured when nanofluids are in a stage of initial development. Therefore, the apparatus and method for measuring the convective heat transfer coefficients of nanofluids according to the present invention can reduce the time and cost required for the manufacturing of samples.

Further, an apparatus for measuring the convective heat transfer coefficients of nanofluids according to the present invention can be implemented as a small-sized structure, and enables the setting of movement velocities of a transfer unit and a sensor unit, so that the convective heat transfer coefficients of a base fluid and a nanofluid can be compared to each other under accurate velocity conditions, thus improving accuracy and reproducibility.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for measuring convective heat transfer coefficients of nanofluids, comprising:
a sensor unit;
a transfer unit disposed on the sensor unit and configured to allow the sensor unit to longitudinally reciprocate in a direction parallel to a ground surface with the sensor unit spaced apart from the ground surface; and
a liquid container arranged below and spaced apart from the sensor unit, and configured to allow a nanofluid or a base fluid, a convective heat transfer coefficient of which needs to be measured, to be put therein, wherein:
a lower portion of the sensor unit is disposed in the nanofluid or the base fluid when the sensor unit longitudinally reciprocates, and
the sensor unit comprises:
a hot wire sensor including a metallic hot wire having a cylindrical shape; a hot wire sensor holder connected to both ends of the hot wire sensor and configured to hold the hot wire sensor in a state parallel to the ground surface;
a sensor unit body disposed on the hot wire sensor holder and having a shape of a bar equipped with hollow spaces therein; and
a support extending upwards from the sensor unit body and configured to connect the sensor unit body to the transfer unit and support both the sensor unit body and the transfer unit.

2. The apparatus according to claim 1, wherein the sensor unit further comprises:
a standard resistor electrically connected to the hot wire sensor; and
a power source configured to supply current both to the standard resistor and to the hot wire sensor.

3. The apparatus according to claim 1, wherein the sensor unit further comprises a data processing device capable of acquiring and storing data measured at the hot wire sensor.

4. The apparatus according to claim 1, wherein the hot wire sensor is coated with Teflon.

5. The apparatus according to claim 1, wherein the hot wire sensor is a platinum hot wire or a tungsten hot wire.

6. The apparatus according to claim 1, wherein the transfer unit comprises:
a transfer unit body longitudinally disposed parallel to the ground surface;
a movable block connected to the sensor unit and configured to longitudinally reciprocate in a direction parallel to the ground surface along the transfer unit body;
a motor disposed at one end of the transfer unit body and configured to reciprocate the movable block by forward/reverse rotation of the motor; and
a motor controller electrically connected to the motor and configured to control rotational speed and rotational direction of the motor.

7. The apparatus according to claim 6, wherein the transfer unit body comprises:
a screw having a shape of a cylinder, a surface of which has a spiral protrusion, and configured to be forwardly/reversely rotated by the motor; and
a guide plate arranged in parallel below and spaced apart from the screw.

8. A method of measuring convective heat transfer coefficients of nanofluids, comprising the steps of:
putting a base fluid or a nanofluid in a liquid container such that a hot wire sensor of a sensor unit is disposed in the base fluid or the nanofluid put in the liquid container;
electrically connecting a power source of a voltage dividing circuit to the hot wire sensor and electrically connecting a data processing device to the hot wire sensor;
driving a motor of a transfer unit to longitudinally reciprocate the hot wire sensor in a direction parallel to a ground surface, when the hot wire sensor is disposed in the base fluid or the nanofluid put in the liquid container;
stopping driving of the motor and interrupting supply of power to the voltage dividing circuit; and analyzing and processing data acquired by the data processing device.

9. The method according to claim 8, wherein the voltage dividing circuit comprises:
- a power source electrically connected to the hot wire sensor and configured to supply the power to the hot wire sensor; and
- a standard resistor electrically connected in series with the hot wire sensor and the power source.

10. The method according to claim 8, wherein the step of driving the motor of the transfer unit is performed such that speed of forward/reverse rotation of the motor can be accurately controlled by a motor controller electrically connected to the motor.

\* \* \* \* \*